United States Patent
Ohashi et al.

(10) Patent No.: US 11,547,725 B2
(45) Date of Patent: Jan. 10, 2023

(54) ANTI-CANCER T CELLS AND THEIR PREPARATION USING COENZYME A

(71) Applicant: UNIVERSITY HEALTH NETWORK, Toronto (CA)

(72) Inventors: Pamela S. Ohashi, Toronto (CA); Michael St. Paul, Richmond Hill (CA); Sam Saibil, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 43 days.

(21) Appl. No.: 16/478,969

(22) PCT Filed: Dec. 21, 2017

(86) PCT No.: PCT/CA2017/000274
§ 371 (c)(1),
(2) Date: Jul. 18, 2019

(87) PCT Pub. No.: WO2018/132890
PCT Pub. Date: Jul. 26, 2018

(65) Prior Publication Data
US 2019/0365813 A1 Dec. 5, 2019

Related U.S. Application Data

(60) Provisional application No. 62/447,491, filed on Jan. 18, 2017.

(51) Int. Cl.
| | |
|---|---|
| *A61K 35/17* | (2015.01) |
| *C12N 5/0783* | (2010.01) |
| *C07K 16/22* | (2006.01) |
| *C07K 16/24* | (2006.01) |
| *C07K 16/28* | (2006.01) |

(52) U.S. Cl.
CPC .............. *A61K 35/17* (2013.01); *C07K 16/22* (2013.01); *C07K 16/241* (2013.01); *C07K 16/247* (2013.01); *C07K 16/249* (2013.01); *C07K 16/2809* (2013.01); *C07K 16/2815* (2013.01); *C12N 5/0636* (2013.01); *C12N 2501/2306* (2013.01); *C12N 2501/25* (2013.01); *C12N 2501/70* (2013.01); *C12N 2501/998* (2013.01)

(58) Field of Classification Search
None
See application file for complete search history.

(56) References Cited

U.S. PATENT DOCUMENTS 6,509,035 B1 * 1/2003 Ren .................. A61K 47/12
514/960

FOREIGN PATENT DOCUMENTS

| | | |
|---|---|---|
| CN | 102397259 | 4/2012 |
| WO | WO200112200 A1 | 2/2001 |

OTHER PUBLICATIONS

Ma and Feng, Int J Mol Sci. Jul. 19, 2016;17(7):1162 (Year: 2016).*
Moyo and Savona, Curr Hematol Malig Rep. Dec. 2016;11(6):441-448 (Year: 2016).*
PCT international Search Report and Written Opinion dated Mar. 28, 2018 re: International Application No. PCT/CA2017/000274.
Res et al.; "Over representation of IL-I7A and IL-22 producing CD8 T cells in lesional skin suggests their involvement in the pathogenesis of psoriasis" PLoS One, Nov. 2010, vol. 5, Issue 11, pp. 1-11.
Liu et al.; "Interleukin-21 induces the differentiation of human Tc22 cells via phosphorylation of signal transducers and activators of transcription", Immunology, Apr. 2011, vol. 32, pp. 540-548.
Chang, Chih-Hao et al; Posttranscriptional Control of T Cell Effector Function by Aerobic Glycolysis, Cell 153 Jun. 6, 2013, pp. 1239-1251; DOI: Org/10.1016/j.cell.2013.05.016.
Crompton, Joseph G. et al, Akt Inhibition Enhances Expansion of Potent Tumor-Specific Lymphocytes with Memory Cell Characteristics, American Association for Cancer Research, Cancer Res; 75(2) Jan. 15, 2015, pp. 296-305 DOI:10.1158/0008-5472. CAN-14-2277.
Gerriets, Valerie, A. et al., Metabolic programming and PDHK1 control CD4 T cell subsets and inflammation, The Journal of Clinical Investigation, Jan. 2015; 125(1); pp. 194-208, DOI: Org/10.1172/JCI76012.
Michalek, Ryan D., et al, Cutting Edge: Distinct Glycolytic and Lipid Oxidative Metabolic Programs Are Essential for Effector and Regulatory CD4+ T Cell Subsets; Journal of Immunology; J Immunol 2011; 186:3299-3303; Prepublished online Feb. 11, 2011; DOI: 10.4049/jimmunol. 1003613 http://www.jimmunol.Org/content/.
Scharping, Nicole E. et al, The Tumor Microenvironment Represses T Cell Mitochondrial Biogenesis to Drive Intratumoral T Cell Metabolic Insufficiency and Dysfunction; Article CellPress, Immunity 45, pp. 1-15 Aug. 16, 2016 DOI: Org/10.1016/j.immuni.2016. 07.009.
Srinivasan, Balaji et al, Extracellular A'-phosphopantetheine is a source for intracellular coenzyme A synthesis article, Nature Chemical Biology, vol. 111 Oct. 2015, pp. 784-795, published online: Aug. 31, 2015, www.nature.com/naturechemicalbiology, DOI: 10.1038/NCHEMBI0.1906.
Tannahill, G.M. et al, Succinate is a inflammatory signal that induces IL-1β through HIF-1a, Nature | vol. 496 | Apr. 11, 2013, pp. 238-243, DOI:10.1038/nature11986, © 2013 Macmillan Publishers Limited.

(Continued)

*Primary Examiner* — Daniel C Gamett
(74) *Attorney, Agent, or Firm* — Norton Rose Fulbright Canada LLP

(57) ABSTRACT

There is described herein, a method for inducing Tc22 lineage T cells from a population of CD8+ T cells, the method comprising: a) providing a population of CD8+ T cells; b) activating the population; and c) culturing or contacting the population of CD8+ T cells with Coenzyme A.

21 Claims, 11 Drawing Sheets
Specification includes a Sequence Listing.

(56) References Cited

OTHER PUBLICATIONS

Zenewicz, Lauren A. et al, Innate and adaptive interleukin-22 protects mice from inflammatory bowel disease, National Institute of Health, Public Access Author Manuscript, Published in final edited form as: Immunity. Dec. 19, 2008; 29(6): pp. 947-957. DOI:10.1016/j.immuni.2008.11.003.

\* cited by examiner

SEQUENCE LISTING

```
<160> NUMBER OF SEQ ID NOS: 2

<210> SEQ ID NO 1
<211> LENGTH: 9
<212> TYPE: PRT
<213> ORGANISM: Lymphocytic choriomeningitis virus

<400> SEQUENCE: 1

Lys Ala Val Tyr Asn Phe Ala Thr Met
1               5

<210> SEQ ID NO 2
<211> LENGTH: 20
<212> TYPE: PRT
<213> ORGANISM: Lymphocytic choriomeningitis virus

<400> SEQUENCE: 2

Gly Leu Asn Gly Pro Asp Ile Tyr Lys Gly Val Tyr Gln Phe Lys Ser
1               5                   10                  15

Val Glu Phe Asp
            20
```

ANTI-CANCER T CELLS AND THEIR PREPARATION USING COENZYME A

RELATED APPLICATION

This application claims priority to U.S. Provisional Patent No. 62/447,491 filed on Jan. 18, 2017, which is hereby incorporated by reference in its entirety.

SEQUENCE LISTING

The Sequence Listing submitted electronically titled "SL-198US_ST25.txt" (702 bytes in size; created on Apr. 13, 2022) is incorporated herein by reference.

FIELD OF THE INVENTION

The invention relates to T cells and specifically, to a IL-22+CD8+ T cell subset with anti-tumor function.

BACKGROUND OF THE INVENTION

Metabolic programming is a central regulator of T cell activation, effector function and differentiation. Upon activation, T cells engage in aerobic glycolysis and increase their rate of glycolysis and lactate production disproportionately to the increase in oxidative phosphorylation (OXPHOS)[1-4] Adoption of this highly glycolytic phenotype supports effector function, as cytokine production is coupled to the flux of glucose down the glycolytic pathway[5-7]. Metabolic pathways also control the differentiation of $CD8^+$ memory cells as wells as the commitment of $CD4^+$ cells to specific subset lineages[8-14].

SUMMARY OF THE INVENTION

In an aspect, there is provided, a method for inducing Tc22 lineage T cells from a population of CD8+ T cells, the method comprising: a) providing a population of CD8+ T cells; b) activating the population; and c) culturing or contacting the population of CD8+ T cells with Coenzyme A.

In an aspect, there is provided, a population of cells comprising Tc22 lineage T cells that are CD8+/IL-22+/IL17-/IFNγlow.

In an aspect, there is provided, a population of Tc22 lineage T cells produced by the method described herein.

In an aspect, there is provided, the population described herein, for use in the treatment of cancer, preferably a cancerous tumor.

In an aspect, there is provided, a method of treating cancer, preferably a cancerous tumor, in a patient, the method comprising administering to the patient the population described herein.

In an aspect, there is provided, a use of the population described herein, in the manufacture of a medicament for the treatment of cancer, preferably a cancerous tumor.

In an aspect, there is provided a method of treating cancer, preferably a cancerous tumor, or an inflammatory disease, comprising administering to the patient Coenzyme A or Coenzyme A treated T cells.

In an aspect, there is provided a use of Coenzyme A or Coenzyme A treated T cells for the treatment of cancer, preferably a cancerous tumor, or an inflammatory disease.

In an aspect, there is provided a use of Coenzyme A or Coenzyme A treated T cells in the manufacture of a medicament for the treatment of cancer, preferably a cancerous tumor, or an inflammatory disease.

BRIEF DESCRIPTION OF FIGURES

These and other features of the preferred embodiments of the invention will become more apparent in the following detailed description in which reference is made to the appended drawings wherein.

DETAILED DESCRIPTION

Figure 1:
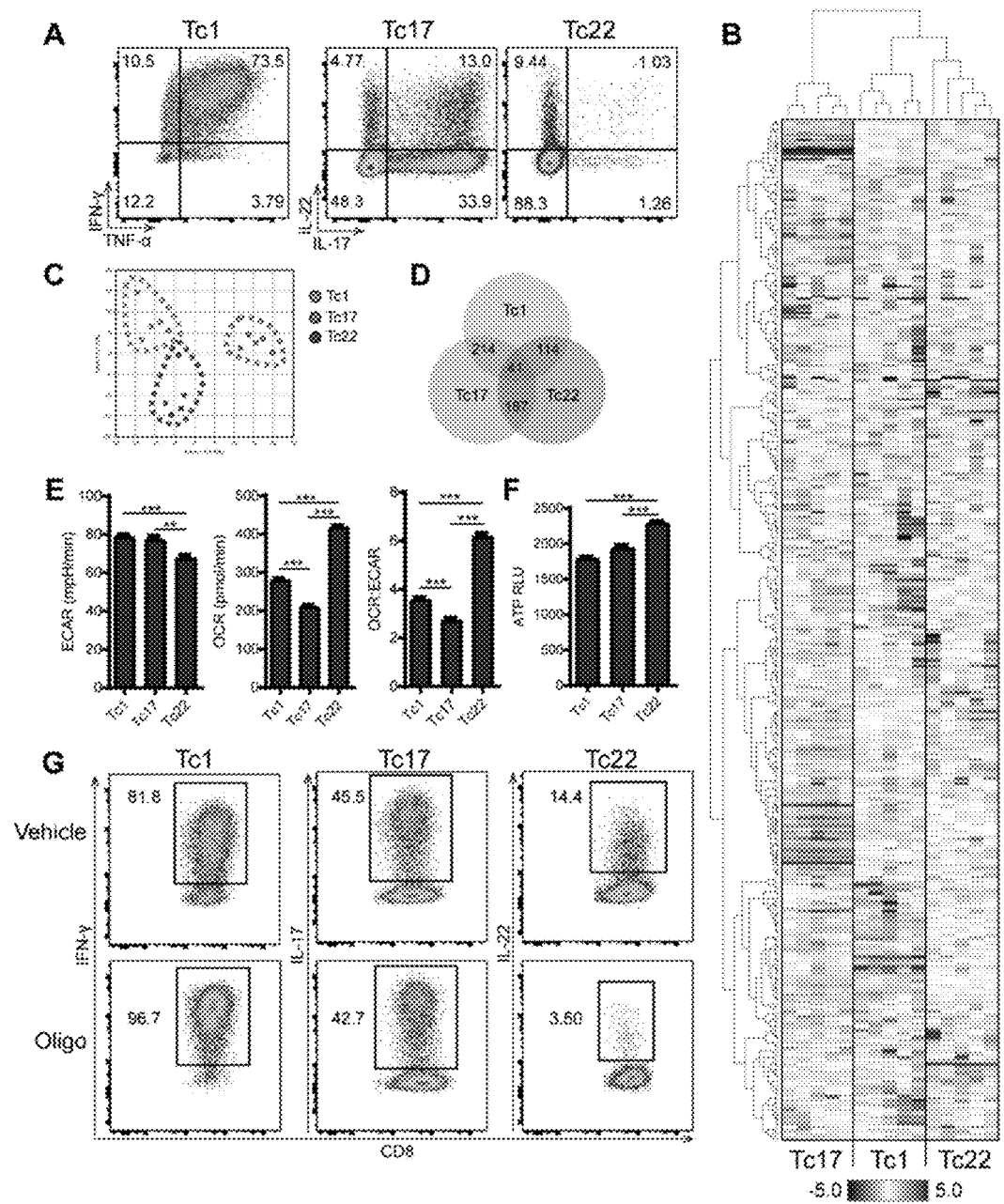
FIG. 1. Tc22s are metabolically distinct and require OXPHOS for polarization. (A) Cytokine profile of CD8+ T cells activated for three days in the presence of polarizing cytokines (B-D) Metabolites were extracted and quantified from polarized Tc subsets derived from 5 mice and displayed as a (B) heatmap or (C) PCA plot. (D) Number of significantly different metabolites relative to each subset. (E) Basal extracellular acidification rate (ECAR), oxygen consumption rate (OCR) and OCR:ECAR as determined by Seahorse Bioanalyzer. (F) ATP levels in polarized Tc subsets. (G) Cytokine profile of CD8+ Tc subsets polarized in the presence of oligomycin (Oligo) or vehicle control. (E,F) Bar graphs are means of (E) 6 or (F) 3 replicates ±SEM. Statistical significance was calculated with one-way ANOVA with a Tukey test. $p<0.01$, *$p<0.001$. (A,E-G) Results shown are representative of at least 2 independent experiments.

In the following description, numerous specific details are set forth to provide a thorough understanding of the invention. However, it is understood that the invention may be practiced without these specific details.

Generally, in one aspect, the present invention is directed to stimulation, activation, or expansion of T cells, including but not limited to CD4+ and CD8+ T cells.

Akin to CD4+ T cells, CD8+ T cells also differentiate into multiple different T cytotoxic (Tc) effector subsets (St. Paul et al., submitted). The metabolic phenotype of the Tc subsets and the impact of metabolism upon their differentiation and function are undefined. Here, we utilize a metabolomics approach to interrogate the metabolic profile of Tc1, Tc17 and Tc22 differentiated CD8+ effector cells and found each subset to possess a unique metabolic signature with Tc22 cells being distinct in that they displayed increased utilization of OXPHOS. This increased OXPHOS was required for Tc22 differentiation, as pharmacological inhibition of OXPHOS abrogated Tc22 differentiation but not Tc1 or Tc17 development. Moreover, we identified coenzyme A (CoA) as a reagent that enhances OXPHOS in CD8+ T cells and promotes Tc22 differentiation. Surprisingly, we found that CoA alone, in the absence of polarizing cytokines, was sufficient to generate CD8+IL-22+ Tc22 cells as well as CD4+ Th22 cells. To our knowledge, this is the first example of an effector T cell population whose differentiation can be induced solely via altering T cell metabolism in the absence of polarizing cytokines.

In an aspect, there is provided, a method for inducing Tc22 lineage T cells from a population of CD8+ T cells, the method comprising: a) providing a population of CD8+ T cells; b) activating the population; and c) culturing or contacting the population of CD8+ T cells with Coenzyme A.

Methods of activating T cells are known in the art, for example, as described in T Cell Activation, Annu. Rev. Immunol. 2009. 27:591-619.

The term "activation", as used herein, refers to the state of a cell following sufficient cell surface moiety ligation to induce a noticeable biochemical or morphological change. Within the context of T cells, such activation refers to the state of a T cell that has been sufficiently stimulated to induce cellular proliferation. Activation of a T cell may also induce cytokine production and performance of regulatory or cytolytic effector functions. Within the context of other cells, this term infers either up or down regulation of a particular physico-chemical process The term "activated T cells" indicates T cells that are currently undergoing cell division, cytokine production, performance of regulatory or cytolytic effector functions, and/or has recently undergone the process of "activation."

In some embodiments, the activation comprises culturing or contacting the population with at least one of (i) anti-CD3 antibody and (ii) gp33 peptide from LCMV (KAVYN-FATM) (SEQ ID NO. 1).

In some embodiments, the population of CD8+ T cells is additionally cultured or contacted with TNF-α or IL-6.

In some embodiments, the population of CD8+ T cells is additionally cultured or contacted with aryl hydrogen receptor (AhR) agonist, preferably 6-Formylindolo(3,2-b)carbazole (FICZ).

In some embodiments, the population of CD8+ T cells is additionally cultured or contacted with anti-IFNγ antibody.

In some embodiments, the population of CD8+ T cells is additionally cultured or contacted with anti-TGF-β antibody.

In some embodiments, the population of CD8+ T cells is additionally cultured or contacted with succinate.

In some embodiments, the population of CD8+ T cells is additionally cultured or contacted with pantothenate.

In some embodiments, the Tc22 lineage T cells are CD8+/IL-22+/IL17-/IFNγlow.

In some embodiments, the Tc22 lineage T cells are additionally IL-4-, IL-5-, IL-9-, IL-10- and/or or IL-13-.

In some embodiments, the Tc22 lineage T cells are additionally TNF-αhi and/or IL-2hi.

In some embodiments, step c) is performed before or after step b). In other embodiments, step c) is performed simultaneously with step b).

In an aspect, there is provided, a population of cells comprising Tc22 lineage T cells that are CD8+/IL-22+/IL17-/IFNγlow.

In an aspect, there is provided, a population of Tc22 lineage T cells produced by the method described herein.

The T cell populations generated herein would be understood to beneficial in treating cancer, and may include adrenal cancer, anal cancer, bile duct cancer, bladder cancer, bone cancer, brain/cns tumors, breast cancer, castleman disease, cervical cancer, colon/rectum cancer, endometrial cancer, esophagus cancer, ewing family of tumors, eye cancer, gallbladder cancer, gastrointestinal carcinoid tumors, gastrointestinal stromal tumor (gist), gestational trophoblastic disease, hodgkin disease, kaposi sarcoma, kidney cancer, laryngeal and hypopharyngeal cancer, leukemia (acute lymphocytic, acute myeloid, chronic lymphocytic, chronic myeloid, chronic myelomonocytic), liver cancer, lung cancer (non-small cell, small cell, lung carcinoid tumor), lymphoma, lymphoma of the skin, malignant mesothelioma, multiple myeloma, myelodysplastic syndrome, nasal cavity and paranasal sinus cancer, nasopharyngeal cancer, neuroblastoma, non-hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer (basal and squamous cell, melanoma, merkel cell), small intestine cancer, stomach cancer, testicular cancer, thymus cancer, thyroid cancer, uterine sarcoma, vaginal cancer, vulvar cancer, waldenstrom macroglobulinemia, and wilms tumor.

In an aspect, there is provided, the population described herein, for use in the treatment of cancer, preferably a cancerous tumor.

In an aspect, there is provided, a method of treating cancer, preferably a cancerous tumor, in a patient, the method comprising administering to the patient the population described herein.

In an aspect, there is provided, a use of the population described herein, in the manufacture of a medicament for the treatment of cancer, preferably a cancerous tumor.

In an aspect, there is provided a method of treating cancer, preferably a cancerous tumor, or an inflammatory disease, comprising administering to the patient Coenzyme A or Coenzyme A treated Tcells. In some embodiments, the inflammatory disease is a gastro-intestinal inflammatory disease, preferably colitis or inflammatory bowel disease.

In an aspect, there is provided a use of Coenzyme A or Coenzyme A treated Tcells for the treatment of cancer, preferably a cancerous tumor, or an inflammatory disease.

In an aspect, there is provided a use of Coenzyme A or Coenzyme A treated Tcells in the manufacture of a medicament for the treatment of cancer, preferably a cancerous tumor, or an inflammatory disease.

As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

The advantages of the present invention are further illustrated by the following examples. The examples and their particular details set forth herein are presented for illustration only and should not be construed as a limitation on the claims of the present invention.

EXAMPLES

Materials and Methods:

Mice

C57BL/6 were purchased from The Jackson Laboratory and Taconic. LSL-HIF-1a-dPA mice (JAX strain 009673) were obtained from The Jackson Laboratory and bred to Vav-Cre mice to generate HIF-1α-Transgenic mice. The HIF-1a in these mice has a proline to alanine substitution rendering HIF-1a resistant to degradation by von Hippel Lindau only in cells that express Cre recombinase (22). Generation of P14 mice, which express a transgenic TCR specific for the H2-db gp33 peptide of the lymphocytic choriomeningitis virus (LCMV) was described previously (27). SMARTA mice have been described previously (28).

All mice were maintained at the Ontario Cancer Institute animal facility according to institutional guidelines and with approval of the Ontario Cancer Institute Animal Ethics Committee.

Tc Subset Polarization

P14 CD8+ T cells were magnetically purified (Miltenyi Biotec) and co-cultured with mature bone marrow dendritic cells (BMDCs) pulsed with gp33 peptide from LCMV (KAVYNFATM) (SEQ ID NO. 1) (29) for three days in IMDM (Gibco) supplemented with 10% FCS, L-glutamine, β-mercaptoethanol, penicillin and streptomycin. For CD4+ T cells, SMARTA CD4$^+$ cells were co-cultured for three to four days with BMDCs pulsed with gp61 from LCMV (GLNGPDIYKGVYQFKSVEFD) (SEQ ID NO. 2). To generate Tc or Th subsets, polarizing cocktails were added at the start of the co-culture as follows −Tc1: IL-12 (5 ng/mL), Tc17: IL-6 (20 ng/mL)+TGF-β1 (3 ng/mL)+IL-23 (10 ng/mL)+α-IFN-γ (XMG1.2-10 µg/mL), and Tc22: IL-6 (20 ng/mL)+TNF-α (40 ng/mL)+6-Formylindolo(3,2-b)carbazole (FICZ at 2 ng/mL)+α-IFN-γ (10 µg/mL)+α-TGF-β (1D11.16.8-10 µg/mL). Cytokines and neutralizing antibodies were purchased from Biolegend, eBioscience and R&D. FICZ was purchased from Enzo Life Sciences.

Flow Cytometry, Antibodies and Cytokine Assays

Antibodies used for flow cytometry were purchased from eBioscience, Biolegend and BD Pharmingen. Antibody clones used were: CD4 (RM-45), CD8 (53-6.7), IL-22 (IL22JOP and Poly5164), IL-17 (eBio17B7), IFN-γ (XMG1.2) and TNF-α (MP6-XT22). Antibodies used for western blotting were HIF-1a (Caymen Chem-10006421) and β-actin (Sigma—A2066). For intracellular cytokine staining, cells were re-stimulated for 5-6 hours with Cell-Stimulation Cocktail (eBioscience) in the presence of Brefeldin A (eBioscience), followed by staining using Cytofix/Cytoperm (BD Pharmingen). Flow cytometry data was acquired on a FACSCanto II (BD) and analyzed using FlowJo software (Tree Star). Cytokines were quantified in the supernatant using LEGENDPLEX cytometric bead array (Biolegend) or by ELISA (eBioscience)

Metabolomic Profiling

Metabolomic and statistical analyses were conducted at Metabolon (Durham, N.C.) as described previously (17). Briefly, cell pellets (n=5 biological replicates per group) were disrupted using a GenoGrinder (675 strokes/minute, 2 minutes) and subjected to methanol extraction. Extracts were split into four aliquots and processed for analysis by ultra-high performance liquid chromatography/mass spectrometry (UHPLC/MS) in the positive (two methods), negative or polar ion mode. Metabolites were identified by automated comparison of ion features to a reference library of chemical standards followed by visual inspection for quality control. For statistical analyses and data display, any missing values were assumed to be below the limits of detection; these values were imputed with the compound minimum (minimum value imputation). To determine statistical significance, Welsh's two-factor t-test was performed on protein-normalized data in ArrayStudio (Omicsoft) or "R" to compare data between experimental groups; p<0.05 was considered significant. An estimate of the false discovery rate (Q-value) was calculated to take into account the multiple comparisons that normally occur in metabolomic-based studies, with Q<0.05 used as an indication of high confidence in a result. ArrayStudio was also used to generate high level overview display items (PCA, heatmaps). Pathway enrichment scores for Tc22 were calculated relative to control effector CD8+ T cells using the formula: (# of significant metabolites in pathway(k)/total # of detected metabolites in pathway(m))/(total # of significant metabolites(n)/total # of detected metabolites(N)) (k/m)/(n/N). A P-value cut off of p<0.01 was used. Only pathways where at least 3 metabolites were examined were included.

Metabolic Assays and Stable Isotype Tracing Analysis

Seahorse was performed as previously described (11). ATP quantification was performed on day 3 polarized T cells using a commercial kit (Sigma) according to the recommended protocol. For SITA, CD8+ T cells activated for three days in the presence of vehicle or CoA were harvested, washed and incubated for 2.5 hours with U-13C6-glucose (Cambridge Isotopes). Cells were then washed and pellet was frozen in methanol. The cells were thawed on ice and lysed by sonication at 4° C. using a Diagenode Bioruptor (30s. on, 30s off, 5 mins). The resulting mixtures were spun down (15 mins 13000 rpm 4° C.) to remove the cellular debris, the resulting supernatants were transferred to clean microfuge tubes and the solvent was removed using a speed-vac at room temperature. The resulting pellets were stored at −70° C. until derivitization. The pellets were solubilized in 30 µL of pyridine containing methoxyamine (10 mg/mL; Sigma) and each sample was spiked with 1 µL of myristic acid-D27 (750 ng/mL in pyridine; Cambridge Isotopes). The samples were vortexed, sonicated, transferred to autoinjection vials and incubated at room temperature for 30 mins. Subsequent to this, 70 uL of N-tert-Butyldimethylsilyl-N-methyltrifluoroacetamide (MTBSTFA; Sigma) was added and the samples were incubated at 70° C. for 30 mins. GC/MS analysis was performed using an Agilent 5975C GC/MS equipped with a DB-5MS+DG capillary column. 1 uL of sample was injected onto the GC column in splitless mode with an inlet temperature of 280° C. and the data was collected by electron impact set at 70 eV. Helium was used as the carrier gas with a flow rate of 1.55 mL/min. The quadrupole was set at 150° C. and the GC/MS interface at 285° C. The oven program for all metabolite analyses started at 60° C. held for 1 min, then increasing at a rate of 10° C./min until 320° C. Bake-out was at 320° C. for 10 mins and the sample data were acquired in scan mode (1-600 m/z).

The data was analyzed using Agilent MSD-Chemstation interfaced to the NIST11 library. Metabolite identities were further cross-validated to standards (Sigma) run in-house on the same instrument. Mass isotopomer analysis was used to derive the flux data employing in-house algorithms to take into account 13C natural abundances. Integrated ion intensities are reported relative to the myristic acid-D27 internal standard.

Pharmacologic Compounds

Oligomycin, Etomoxir, Diethyl succinate and Calcium-D Pantothenate were purchased from Sigma, and Coenzyme A Trilithium Salt (CoA) and HIF-inhibitor (CAS 934593-90-5) were purchased from EMD Millipore. Oligomycin (100 nm) was added to CD8+ T cells 24 hours after the start of activation, while Etomoxir (40 µm), Pantothenate (8 mM), Diethyl Succinate (14 mM) and HIF-Inhibitor (40 µM) were added at the start of activation. CoA was added at the start of activation unless otherwise indicated at a concentration of 2.5-3.5 mM depending on the lot.

RNA Extraction and Sequencing

RNA was extracted from CD8+ T cells activated for three days in the presence of CoA or Vehicle using Qiagen RNEasy kit. Libraries were prepared using TruSeq Stranded Total RNA kit. Two hundred nanograms from RNA samples were ribosomal RNA depleted using Ribo-zero Gold rRNA beads, following purification the RNA was fragmented. The cleaved RNA fragments were copied into first strand cDNA using reverse transcriptase and random primers. This is followed by second strand cDNA synthesis using RNase H and DNA Polymerase I. A single "A" based were added and adapter ligated followed by purification and enrichment with PCR to create cDNA libraries. Final cDNA libraries were size validated using Agilent Bioanalyzer and concentration validated by qPCR. All libraries were normalized to 10 nM and pooled together. 10 pM of pooled libraries were loaded onto Illumina cBot for cluster generation. Clustered flow cell was then sequenced Pair-end 100 cycles V3 using Illumina HighSeq 2000 to achieve ~30 million reads per sample.

RNA Sequencing Data Analysis

The Tophat (2.0.8b) software suite with Bowtie (2.0.5) was used to align reads to the *Mus musculus* mm10 mouse genome (igenome). RNA_seqc (1.1.7) was used to assess the quality of the aligned data and depletion based on median coverage across transcript length and identities of top expressed transcripts. Samtools (0.1.18) was used to merge aligned technical replicates and sort alignment files. The cufflinks (2.2.1) software suite was used to quantify alignments. Cuffquant was used to quantify individual sample alignments and Cuffnorm was used to normalize quantified data for each group of biological replicates. Cuffdiff was used in conjunction with the R (3.2.2) library CummeRbund (2.10.0) to explore the data at replicate and grouping levels. A custom python script was used to subset data based on an FPKM threshold of 1, and to apply additional thresholds as indicated. GO term analysis was performed using the database for annotation, visualization and integrated discovery (DAVID) bioinformatics resources (30, 31).

The RNA sequencing analysis performed for the figures comparing Tc1, Tc17 and Tc22 was done as previously described (St. Paul et al., submitted).

Tumors and DSS Colitis

For anti-tumor experiments, 8-12 week old female C57BL/6 mice were randomized into different cohorts and inoculated subcutaneously with $4 \times 10^5$ B16F10-gp33 cells and received $0.5 \times 10^6$ polarized CD8+P14 T cells by tail vein infusion 10 days later. Tumor size was continually assessed using calipers until mice reached experimental endpoint (diameter≥1.5 cm or severe ulceration/necrosis). Upon death, mice were given a tumor size of 225 mm² representing the maximum endpoint value of 1.5 cm×1.5 cm.

For DSS-colitis experiments, 8-12 week old female C57BL/6 mice were randomized into different cohorts and colitis was induced using 2.5% DSS (MP Bio) added to the drinking water of mice for 5 consecutive days. CoA (0.5 mg/mL) or vehicle control was added to the drinking water on day 0. On day 5, mice were switched to fresh water without any DSS added, supplemented with either CoA (0.5 mg/mL) or vehicle control.

Human T Cell Experiments

Peripheral blood mononuclear cells were obtained from healthy donors following institutional review board approval. Written informed consent was obtained from all donors who provided the samples. PBMCs were magnetically sorted for naïve T cells (Miltenyi Biotec) and seeded into a 96-well plate previously coated with 5 µg/mL anti-CD3 (eBioscience, clone OKT3). To induce Tc22 polarization, the following antibodies and cytokines were added to culture: 1 µg/mL anti-CD28 (eBioscience, clone CD28.2), 5 µg/mL anti-IFNγ (BioLegend, clone B27), 5 µg/mL anti-IL-4 (BioLegend, clone 8D4-8), 5 µg/mL anti-TGFβ (eBioscience, clone 1D11.16.8), 20 ng/mL IL-6, 10 ng/mL IL-21, 10 ng/mL IL-23, 40 ng/mL TNF-α (All from BioLegend) and 2 ng/mL FICZ. Pantothenate (8 mM) or vehicle control was also added on day 0. Five days later, cells were stimulated with PMA/ionomycin+Brefeldin for 5-6 hours. Cells were then stained and analyzed for intracellular cytokines by flow cytometry.

Statistical Analysis

Statistical significance was calculated using Graphpad Prism as indicated in the figure legends. $p<0.05$ was considered statistically significant. $*p<0.05$, $p<0.01$, $*p<0.001$.

Results and Discussion

Figure 5:
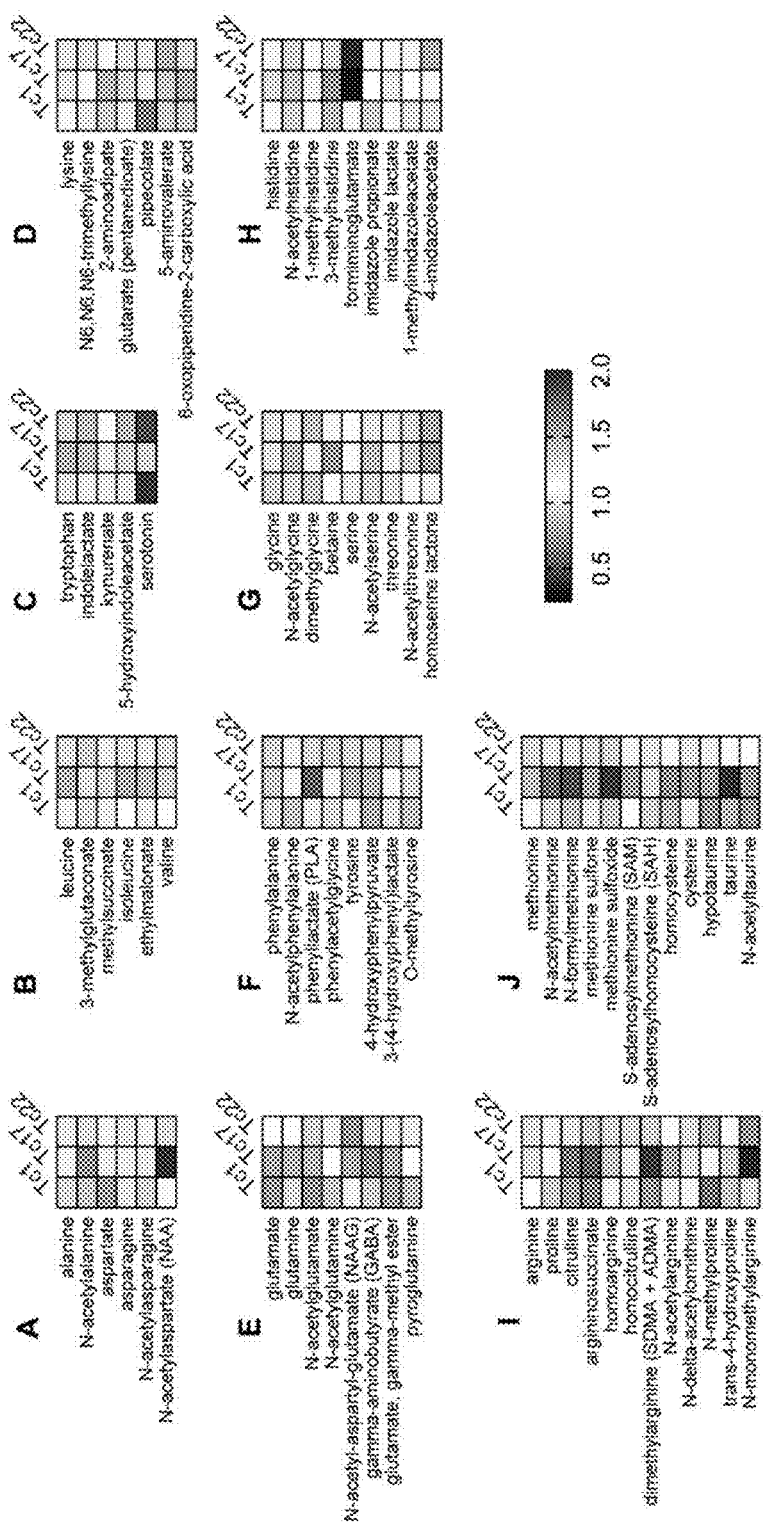
FIG. 5. Evaluation of amino acid metabolism in Tc subsets. Metabolites were quantified in the metabolic pathways of (A) Alanine and Aspartate (B) Leucine, Isoleucine and Valine (C) Tryptothan (D) Lysine (E) Glutamate (F) Phenylalanine and Tyrosine (G) Glycine, Serine and Threonine (H) Histidine (I) Arginine and Proline and (J) Methionine, Cysteine and Taurine metabolic pathways. Results shown are mean scaled intensity of polarized T cells derived from 5 mice as determined by mass spectrometry.
Figure 6:
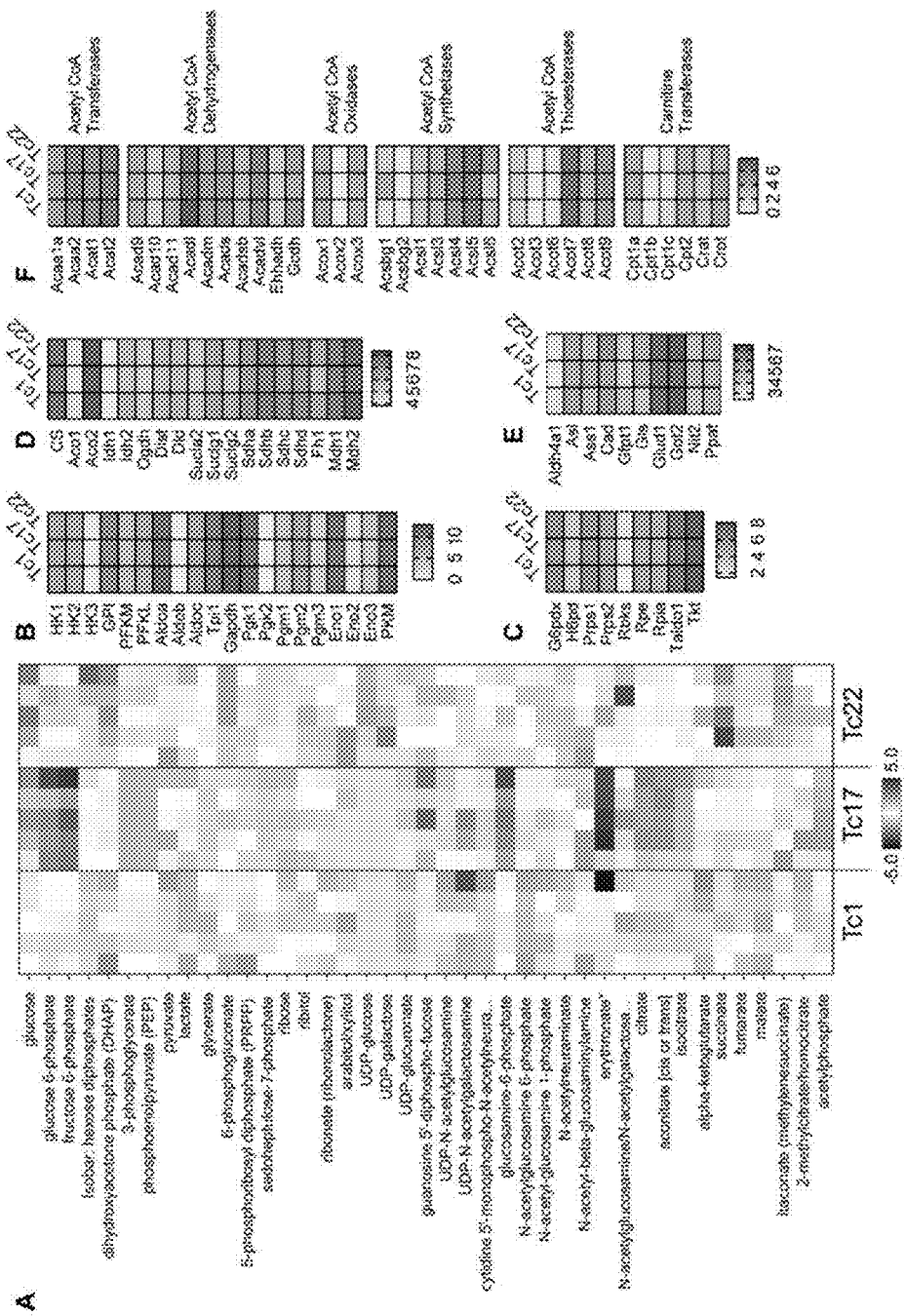
FIG. 6. Tc subsets differentially utilize oxidative and glycolytic pathways. (A) Levels of metabolites involved in glycolysis, nucleotide metabolism and TCA cycle from CD8+ T cells activated for three days in Tc1, Tc17 and Tc22 conditions as determined by mass spectrometry. Each column represents an individual mouse. (B-F) Transcript levels in different CD8+ Tc subsets of genes involved in (B) glycolysis (C) pentose phosphate pathway (D) TCA cycle and (E) glutamine metabolism. Results shown are mean log 2 FPKM+1 values from day 3 polarized CD8+ T cells derived from three mice as determined by RNA sequencing.

To start, we differentiated Tc1, Tc17 and Tc22 cells in vitro (FIG. 1A) and employed an untargeted global metabolomics approach to interrogate their metabolic profiles (FIG. 1B). The intracellular abundance of over 400 metabolites in each Tc subset was quantified using established liquid chromatography-mass spectrometry protocols (17). Using principal component analysis (PCA) and unsupervised hierarchical cluster analysis, we found that each Tc subset formed a unique cluster with Tc17s being the most metabolically distinct, while Tc1s and Tc22s appeared more similar to each other (FIG. 1B,C). Each Tc subset, however, was clearly separate as there were at least 100 metabolites whose levels were significantly altered between each individual subset (FIG. 1D). Assessing the major macromolecular components of metabolism, there were fewer differences in amino acid metabolism between the Tc subsets (FIG. 5) relative to the differences in nucleotide and carbohydrate metabolism (FIG. 6). Some of the most notable differences in metabolites were in the levels of glycolytic and tricarboxylic acid (TCA) cycle intermediates, despite having minimal alterations of these pathways at the transcript levels (FIG. 6). Thus, these data confirmed a unique metabolic profile for Tc1, Tc17 and Tc22 cells and suggested that differences in glycolytic and oxidative metabolism may underpin the Tc1, Tc17 and Tc22 phenotypes.

To further characterize these observed differences in each Tc subset, we analyzed their respective utilization of glycolysis versus OXPHOS using the Seahorse Bioanalyzer. This method allows the concurrent measurement of the oxygen consumption rate (OCR—indicative of OXPHOS) and the extracellular acidification rate (ECAR—indicative of glycolysis) in real-time. Interestingly, we found that the Tc22 subset had the highest OCR rates and the highest ratio of OCR to ECAR amongst the three subsets (FIG. 1E), similar to what has previously been reported for memory CD8$^+$ T cells relative to activated effector cells (11). Consistent with the increased ATP yield of oxidative metabolism compared to glycolysis, Tc22s had the highest amounts of intracellular ATP (FIG. 1F). We also observed metabolites involved in the TCA cycle and OXPHOS, particularly succinate, to be increased in Tc22s (FIG. 6).

Figure 7:
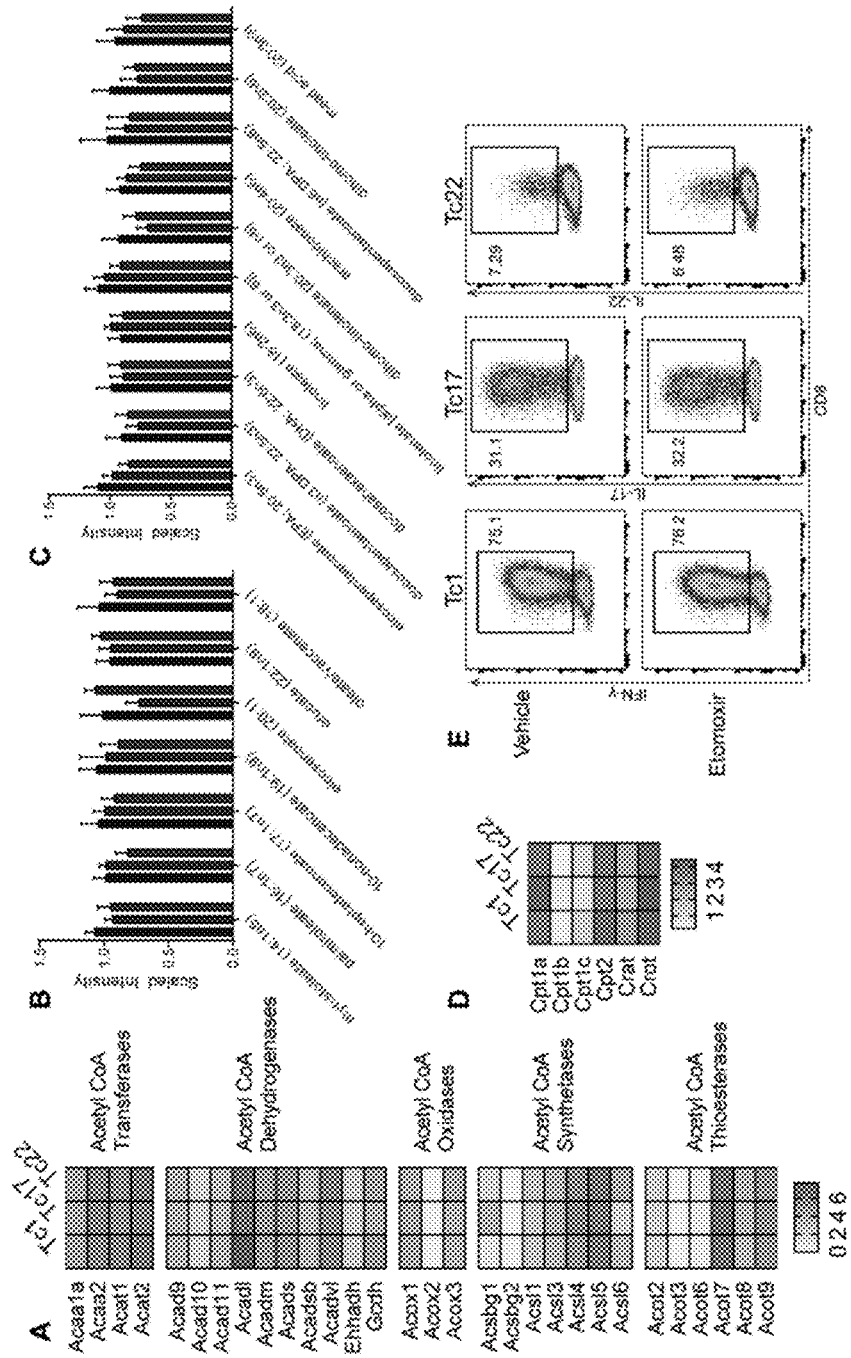
FIG. 7. Tc22 polarization is not dependent on fatty acid metabolism. (A) Transcript levels of genes involved in fatty acid metabolism in Tc subsets. Levels of (B) Long chain and (C) Polyunsaturated fatty acids in Tc1 (blue), Tc17 (black) and Tc22 (red) subsets. (D) Expression levels of genes involved in fatty acid transport. (E) Cytokine expression in CD8+ T cells that were polarized in the presence of etomoxir (40 μm) or vehicle control. (A,D) Results shown are mean log 2 FPKM+1 values from 3 mice as determined by RNA sequencing or (B,C) Mean metabolite levels as determined by mass spectrometry from polarized T cells derived from 5 mice ±standard error.

Given the increased utilization of OXPHOS by Tc22s, we tested whether Tc22 polarization was dependent on this metabolic shift. After activating cells in Tc22 conditions in the presence of oligomycin, an inhibitor of oxidative metabolism, we noted a decrease in Tc22 polarization (FIG. 1G). In contrast, oligomycin did not affect Tc17 polarization but did enhance Tc1 polarization, which is consistent with published reports linking glycolytic metabolism to the production of IFN-γ (5) (FIG. 1G). Interestingly, treatment with the carnitine palmitoyltransferase 1a (CPT1a) inhibitor etomoxir had no effect on Tc22 polarization, indicating that Tc22 polarized cells do not depend on fatty acid oxidation (FAO) to fuel OXPHOS (FIG. 7). This distinguishes the metabolic program of Tc22s from other oxidative T cell lineages, such as CD8+ memory cells and CD4+ T-regs, which have been reported to rely on FAO for their differentiation (8-10). Collectively, these data demonstrate that enhanced utilization of oxidative metabolism is a distinct metabolic phenotype of Tc22 cells as compared to Tc1 and Tc17 effector cells.

Figure 2:
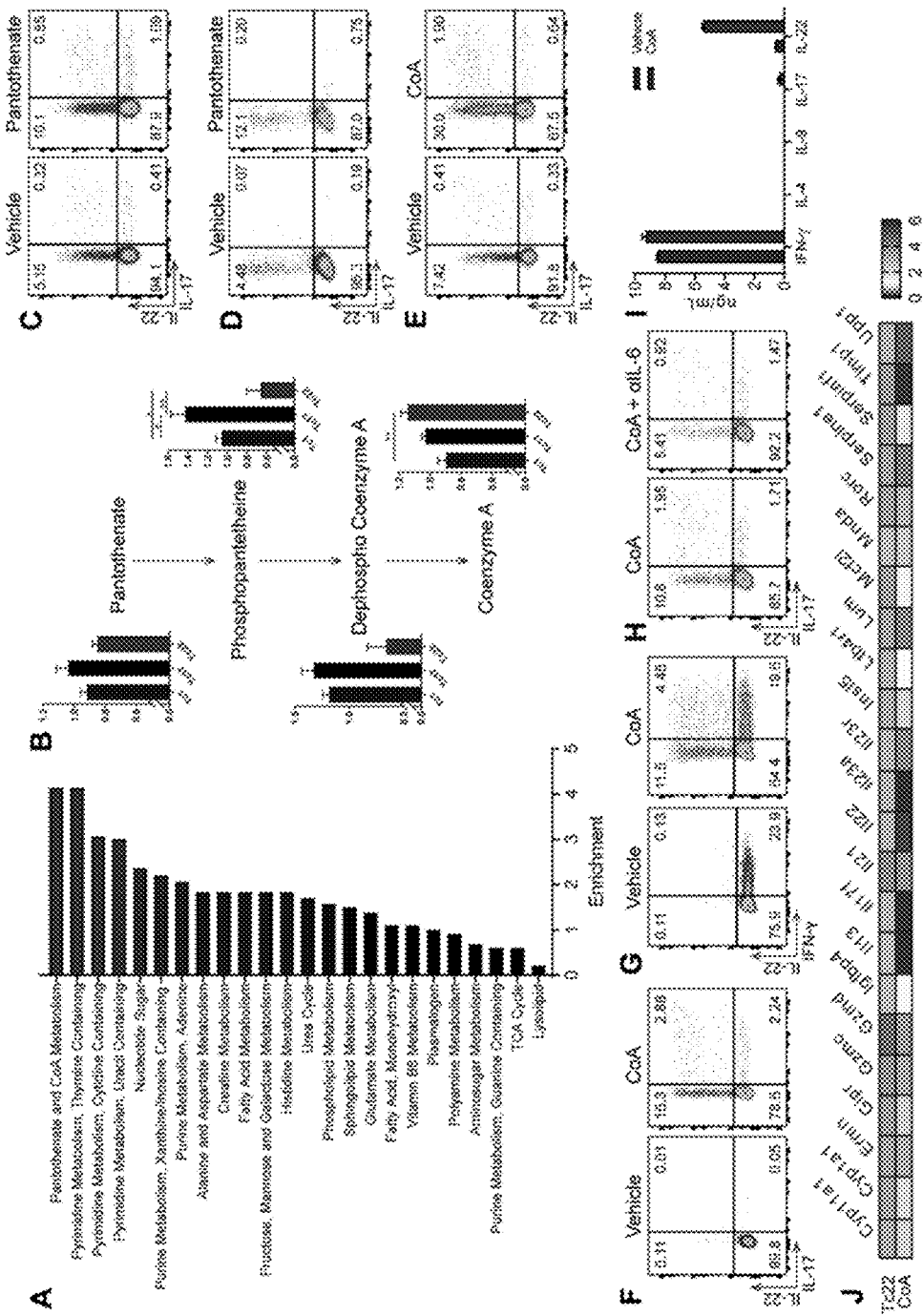
FIG. 2. CoA induces Tc22s in the absence of polarizing cytokines. (A) Metabolic pathways enriched in CD8+ Tc22s (B) Quantification of pantothenate pathway metabolites in Tc subsets. Results shown are mean scaled intensity of metabolites as determined by mass spectrometry ±standard error (N=5) (C,D) Cytokine expression in (C) mouse and (D) human CD8+ T cells activated in Tc22 conditions plus vehicle or pantothenate. (E) Cytokine expression in CD8+ T cells activated in Tc22 conditions plus vehicle or CoA for three days. (F,G) Cytokine expression in CD8+ T cells activated in non-polarizing conditions plus vehicle or CoA. (H) CD8+ T cells were activated for three days in the presence of CoA with or without anti IL-6 (10 ug/mL). (I) Cytokines were quantified in supernatants collected after a three day culture with CD8+ T cells activated in the presence of vehicle or CoA. Results shown are mean±standard error (N=2) (J) Expression level of top significantly up-regulated genes in Tc22s as determined by RNA seq. Values are expressed as mean fold change from 3 mice relative to vehicle treated control cells on a log 2 scale. (B) Statistical significance was calculated using Welch's two tailed t-test adjusted for multiple comparisons *p 50.05, **p 50.01. (C-I) Results shown are representative of at least 2 independent experiments.

To further investigate the metabolic profile of Tc22s, we performed metabolic pathway analysis and found the most enriched pathway to be that of pantothenate/coenzyme A (CoA) (FIG. 2A). This pathway produces the metabolic cofactor CoA from pantothenate through a series of metabolic intermediates. Many of these intermediates were downregulated in Tc22s, while CoA itself was elevated, thereby suggestive of an increased flux of pantothenate to generate CoA (FIG. 2B). Hypothesizing that pantothenate may therefore facilitate Tc22 differentiation, we added exogenous pantothenate during Tc22 polarization and noted enhanced polarization in both mouse (FIG. 2C) and human (FIG. 2D) CD8+ cells. This indicated that the pantothenate pathway can be targeted to enhance Tc22s and IL-22 production.

Figure 8:
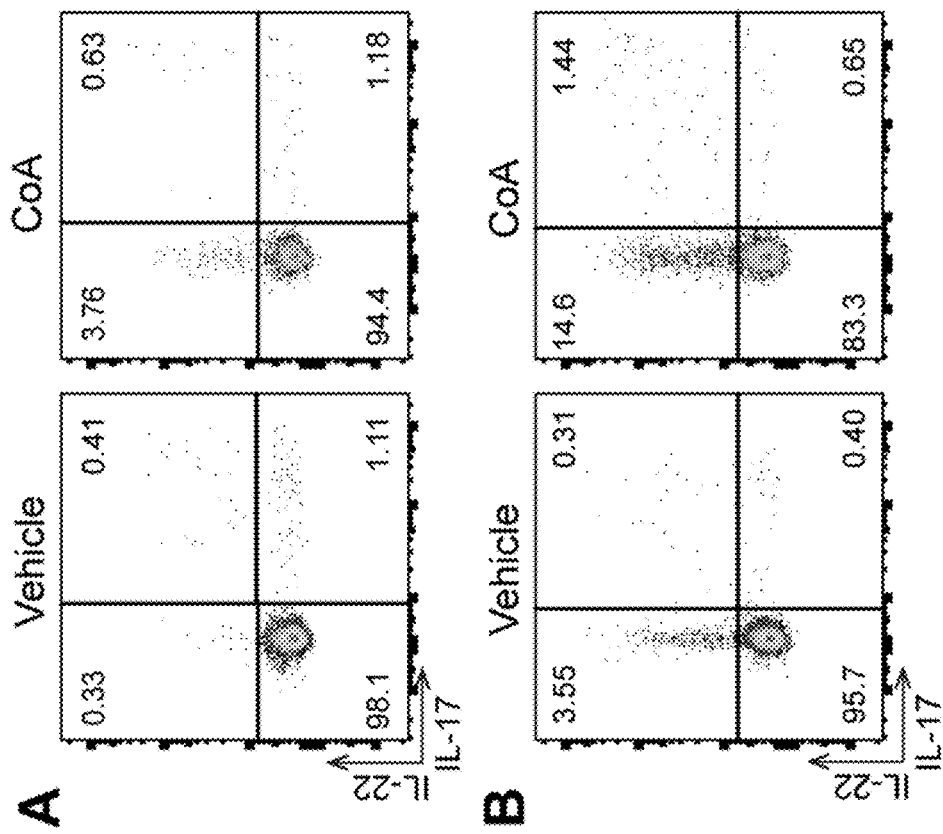
FIG. 8. CoA acts directly on CD8+ T cells to induce or enhance Tc22 polarization. Cytokine expression in CD8+ T cells that were activated using platebound anti-CD3 (5 ug/mL) and soluble anti CD28 (1 ug/mL) for three days in (a) non-polarizing conditions or (b) Tc22 conditions. CoA or vehicle was added 24 hours after the start of activation.

As several steps are required to generate CoA from pantothenate, we wondered whether targeting the pathway downstream of pantothenate may prove to be more effective, as this may bypass any rate-limiting steps. CoA itself provides an attractive target in this context, given that recent evidence indicates that cells can uptake extracellular CoA (18). Indeed, we found that the addition of exogenous CoA during Tc22 polarization greatly enhanced polarization, more so than what we observed for pantothenate (FIG. 2E). Surprisingly, we found that CD8+ T cells activated in the presence of CoA alone skewed primarily towards an IL-22+ IL-17− IFNγ− population in the absence of polarizing cytokines (FIG. 2F,G). This was dependent on the direct interaction of CoA with the T cells, and not the antigen presenting cells (APC) used to activate the T cells, as CoA induced and enhanced Tc22 polarization in an APC-free system (FIG. 8). CoA also functions independent of IL-6, the cytokine that drives the Tc22 lineage, as CoA retained the ability to induce Tc22s despite the presence of an IL-6 neutralizing antibody (FIG. 2H).

To further confirm that CoA was inducing the full Tc22 phenotype, we evaluated the cytokine profile of CoA treated cells and found them to primarily up-regulate IL-22 and none of the other Tc subset lineage-defining cytokines (FIG. 2I). We also performed RNA sequencing on CoA treated cells to determine if they resembled cytokine-induced Tc22s at the level of the transcriptome. Indeed, vast majority of genes up-regulated by Tc22 polarizing cytokines, the "Tc22 signature", were also strongly up-regulated by CoA alone (FIG. 2J). These genes include granzyme C and D, which we previously observed to be expressed highly by Tc22s relative to other Tc subsets (St. Paul et al., submitted). Together, these findings establish that CoA acts on CD8+ T cells to induce the Tc22 phenotype both at a functional and transcriptional level. To our knowledge, we have discovered the first instance in which adding a pharmacologic compound can induce a T cell subset without the need for any polarizing cytokines.

Figure 3:
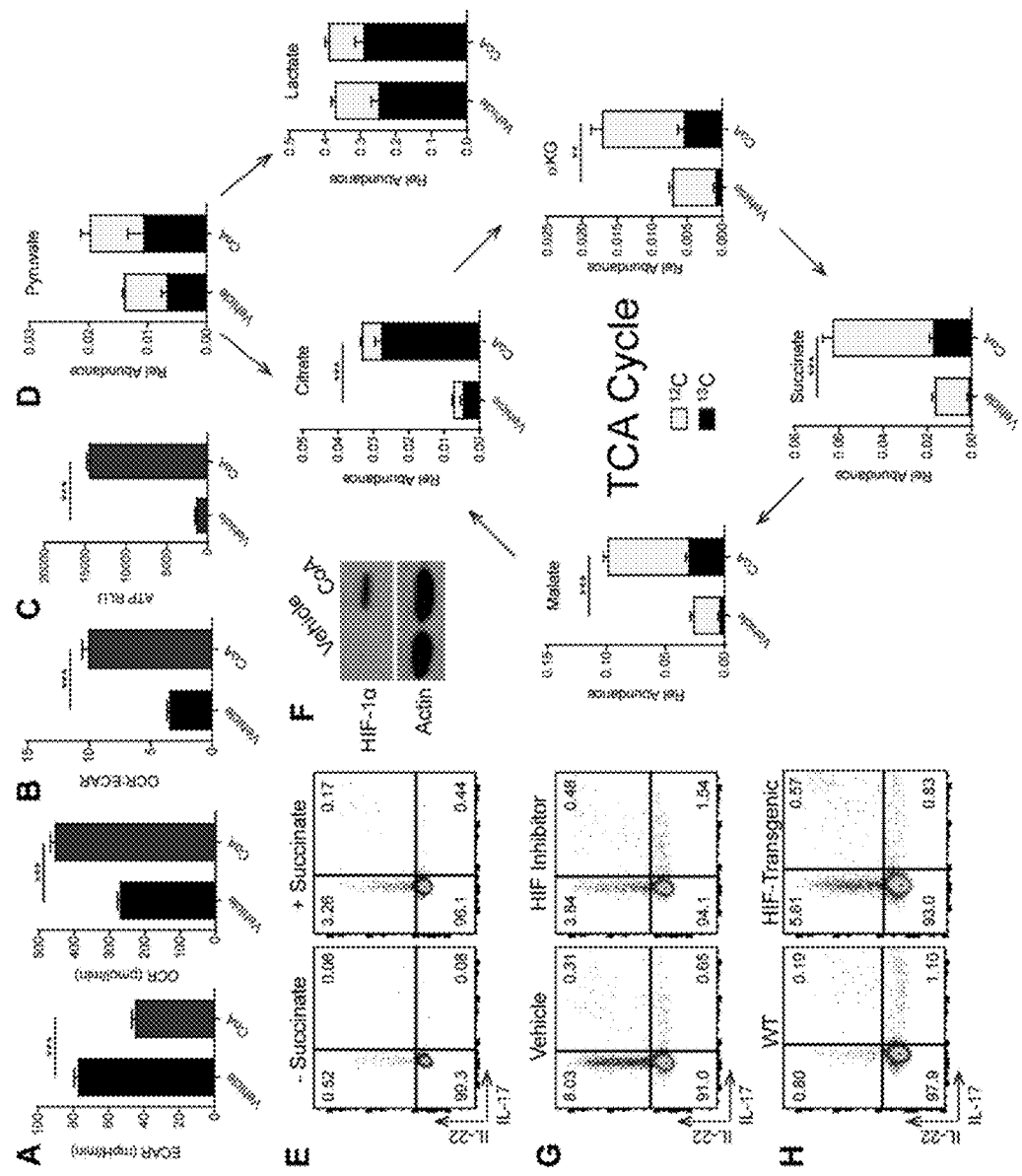
FIG. 3. Oxidative HIF signaling mediates the induction of Tc22s by CoA. Basal (A) OCR, ECAR and (B) OCR:ECAR ratio quantified by Seahorse of CD8+ T cells activated in the presence of vehicle or CoA. (C) ATP levels in CoA treated CD8+ T cells. (D) CD8+ T cells activated for three days in presence of CoA or Vehicle were incubated for 2.5 hours in media containing $^{13}C$ glucose and analyzed by mass spectrometry. (E) CD8+ T cells were activated for three days with or without exogenous succinate added. (F) Western blotting for HIF-1a and β-actin in CD8+ T cells activated in the presence of vehicle or CoA. (G) Cytokine expression in CD8+ T cells that were activated in the presence of CoA and either a HIF inhibitor or vehicle control. (H) WT or HIF-Transgenic CD8+ T cells were activated for three days in non-polarizing conditions using anti-CD3 (5 μg/mL) and anti-CD28 (1 μg/mL). Results shown are (A-C) mean replicates (N=3-6) ±SEM, or (D) means of triplicates ±SEM of activated T cells pooled from 3 mice. Statistical significance was calculated with two-tailed t test. p<0.01, *p<0.001. (A-C, E-H) are representative of at least 2 independent experiments.
Figure 9:
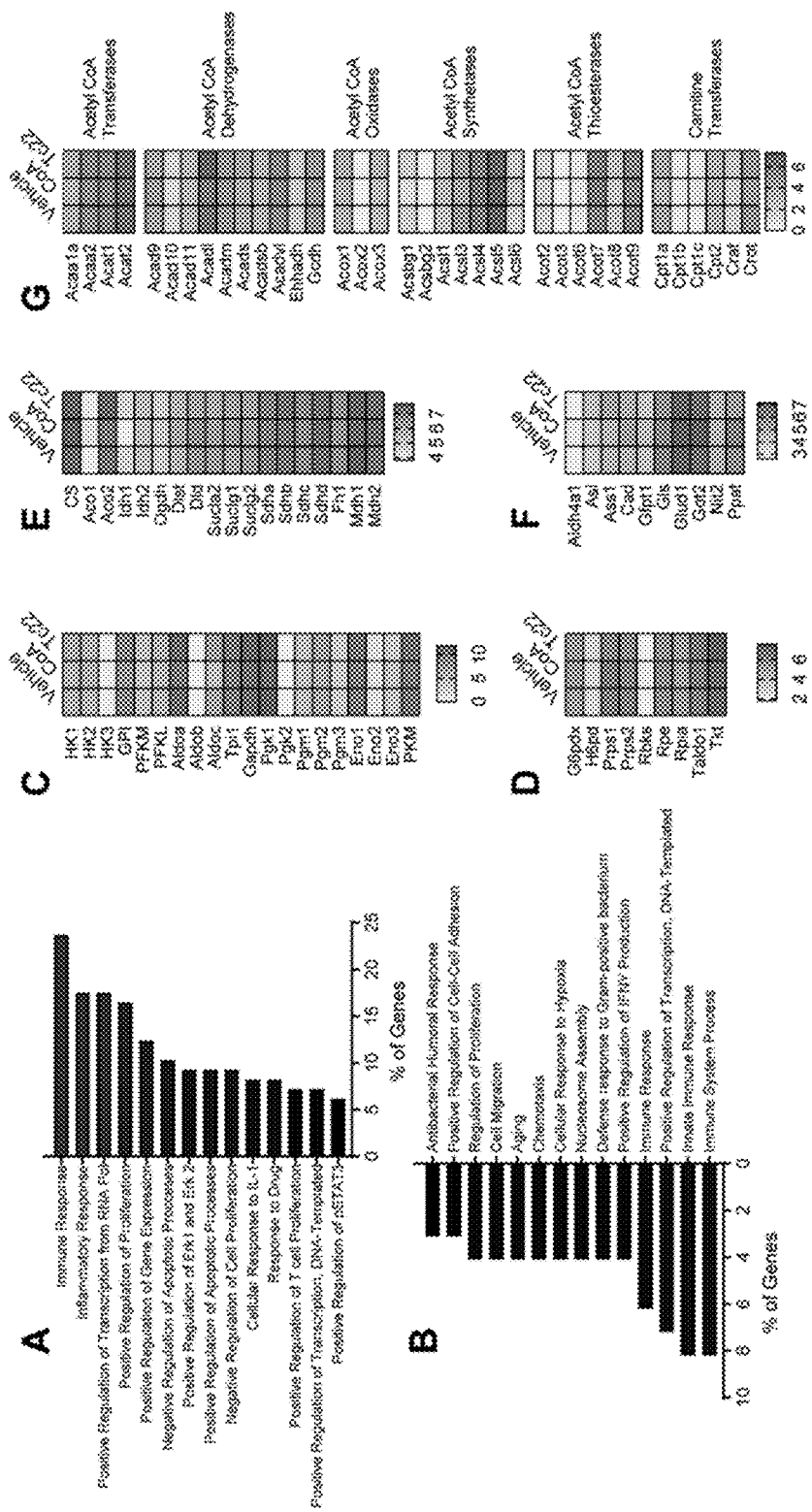
FIG. 9. CoA primarily alters immune and not metabolic genes. GO term analysis of top 100 genes in CD8+ T cells significantly (A) up-regulated and (B) downregulated by CoA treatment as determined by RNA seq. (C-G) Transcript levels in CD8+ T cells activated in the presence of vehicle, CoA or Tc22 conditions genes involved in (C) glycolysis (D) pentose phosphate pathway (E) TCA cycle (F) glutamine and (G) fatty acid metabolism. Results shown are mean log 2 FPKM+1 values from three mice as determined by RNA sequencing.

We found that the enhanced utilization of OXPHOS was a defining metabolic requirement for cytokine-induced Tc22 cells (FIG. 1). Similar to polarizing cytokines (FIG. 6), however, CoA treatment primarily altered the expression of immune system genes and not metabolic genes (FIG. 9). Therefore, by transcriptional analysis, it was unclear if CoA treatment resulted in the same metabolic shift to OXPHOS required by polarizing cytokines to induce the Tc22 lineage. Metabolic analysis of CoA treated cells revealed that they also had a higher basal OCR and a lower basal ECAR compared to vehicle controls (FIG. 3A). This resulted in a high OCR:ECAR ratio for the CoA-treated cells (FIG. 3B). Treatment with CoA also increased intracellular levels of ATP relative to vehicle treated controls (FIG. 3C). These data indicated that CoA promoted an oxidative phenotype similar to what we had described for cytokine-induced Tc22s.

To further characterize this oxidative phenotype of the CoA treated cells, we employed stable isotope tracer analysis (SITA) with $^{13}$C-glucose to track glucose utilization by the cells. We found that CoA treatment resulted in enhanced incorporation of the $^{13}$C label into TCA metabolites, consistent with an increased flux of glucose into the TCA cycle (FIG. 3D). Interestingly, CoA treatment also increased total intracellular pools of many of the TCA intermediates, including succinate. It has previously been demonstrated that succinate can stabilize and activate the transcription factor hypoxia inducible factor (HIF)-1α under normal oxygen tensions (19, 20), and that activation of HIF-1a can promote IL-22 production in CD4+ T cells (21). Thus, we hypothesized that the mechanistic link between OXPHOS and the induction of Tc22s was the succinate-induced activation of HIF-1a signaling in an oxidative environment downstream of CoA or polarizing cytokines. Consistent with this hypothesis, we noted enhanced IL-22 production in CD8+ T cells activated in the presence of succinate (FIG. 3E). Moreover, CoA treated CD8+ T cells had substantially increased levels of HIF-1α (FIG. 3F), and blocking HIF-1a activity inhibited the ability of CoA to induce Tc22s (FIG. 3G). Furthermore, we demonstrated that the activation of CD8+ T cells that constitutively express HIF-1a (22) induced IL-22 production in the absence of polarizing cytokines (FIG. 3H). Together, these findings indicated that the oxidative metabolic phenotype induced by CoA is required to generate succinate and activate HIF-1a signaling to facilitate the polarization of Tc22s.

Figure 10:
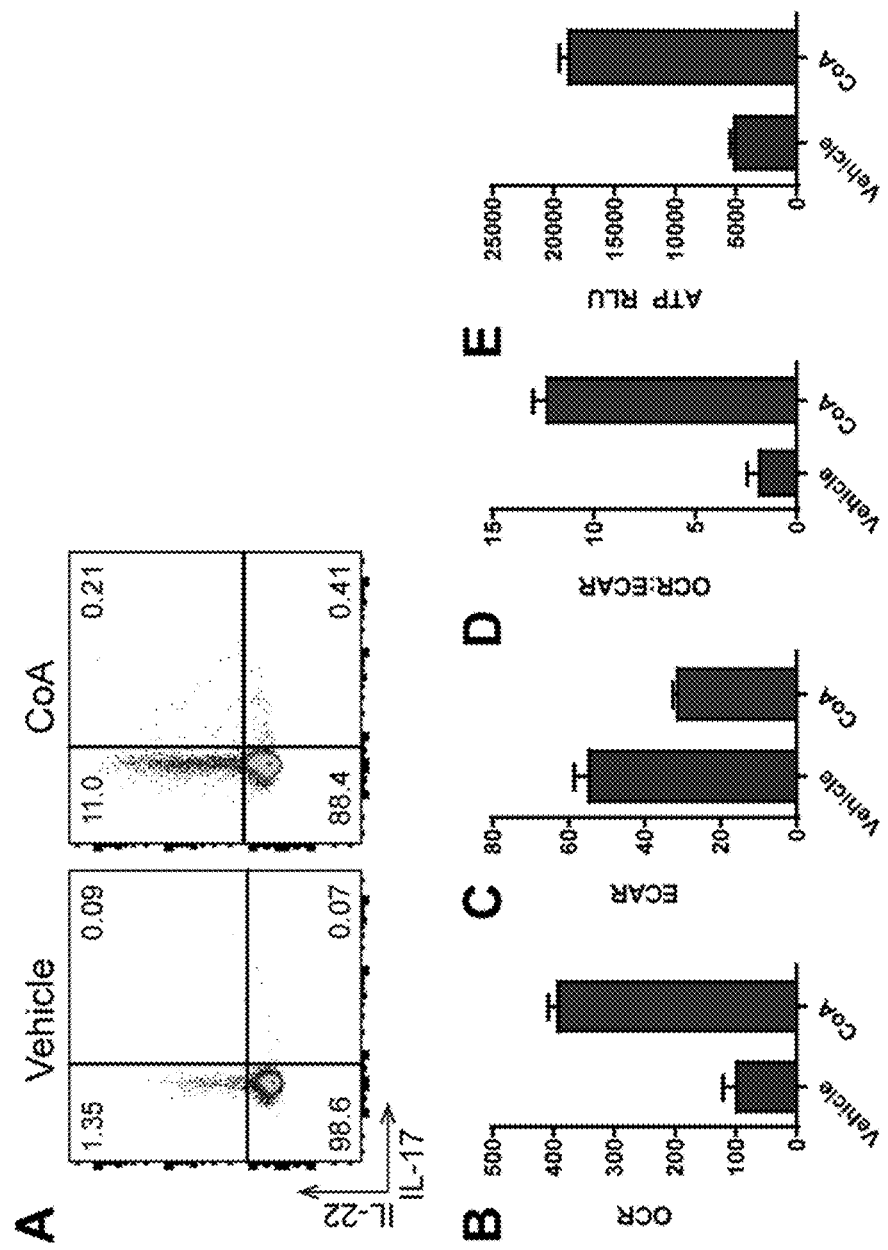
FIG. 10. CoA induces IL-22 and OXPHOS in previously activated effectors. (A) Cytokine profile (B) OCR (C) ECAR, (D) OCR:ECAR ratio and (E) ATP Production was evaluated in previously activated CD8+ T cells that were re-stimulated for 48 hours with anti-CD3 in the presence of vehicle or CoA. (B-E) Results shown are mean values of 3-6 replicates ±standard error.
Figure 11:
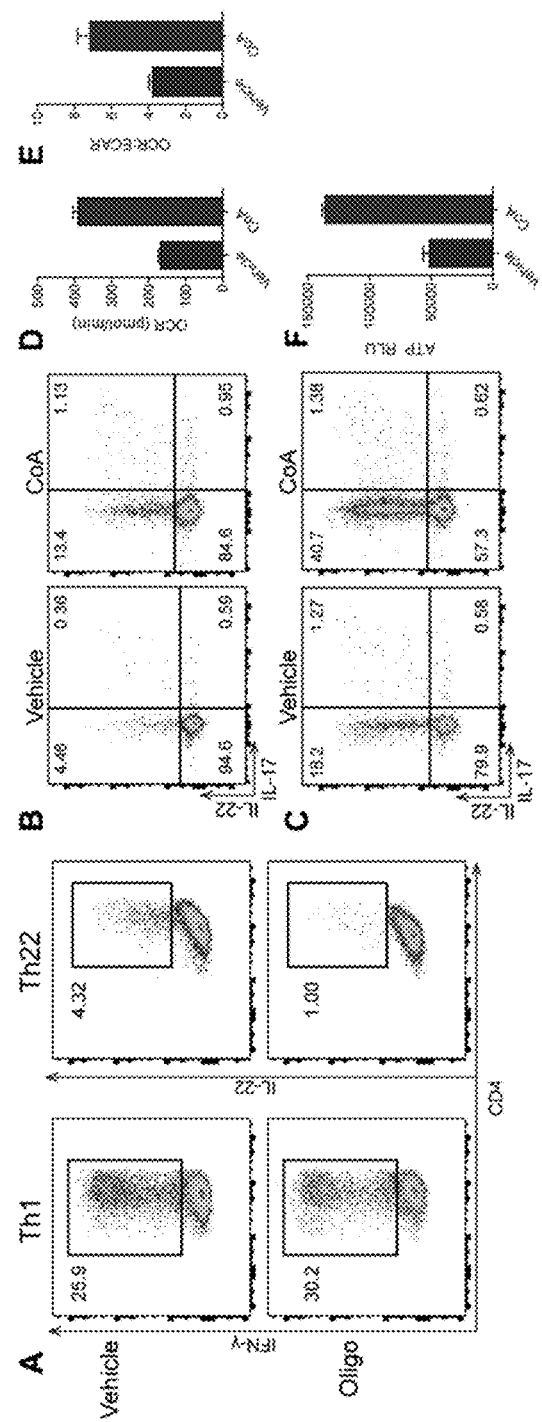
FIG. 11. CD4+ Th22s require OXPHOS and can be induced with CoA. (A) Cytokine profile in CD4+ T cells activated in Th1 or Th22 conditions with vehicle control or Oligomycin (B,C) Cytokine expression in SMARTA CD4+ T cells activated in the presence of vehicle or CoA in (B) non-polarizing or (C) Th22 conditions. (D) OCR, (E) OCR:ECAR ratio and (F) ATP production was evaluated in CD4+ T cells activated in the presence of vehicle or CoA. (D-F) Results shown are mean values of 3-4 replicates ±standard error.

Having found that the addition of CoA could polarize naïve cells to Tc22s during activation, we investigated the effects of CoA on previously activated CD8+ T cells. The addition of CoA during a secondary re-stimulation of CD8+ T cells previously activated in the absence of polarizing cytokines was able to induce IL-22 production and promote an oxidative phenotype (FIG. 10). The effects of CoA were not only limited to CD8+ T cells, as we also demonstrated that CD4+ Th22s are dependent on OXPHOS for polarization (FIG. 11A) and that CoA similarly induced and enhanced Th22 polarization by providing a metabolic shift towards OXPHOS and enhanced ATP production (FIG. 11B-F). Together, these findings demonstrate the versatility of CoA and its ability to induce OXPHOS and IL-22 producing T cell subsets in different contexts.

Figure 4:
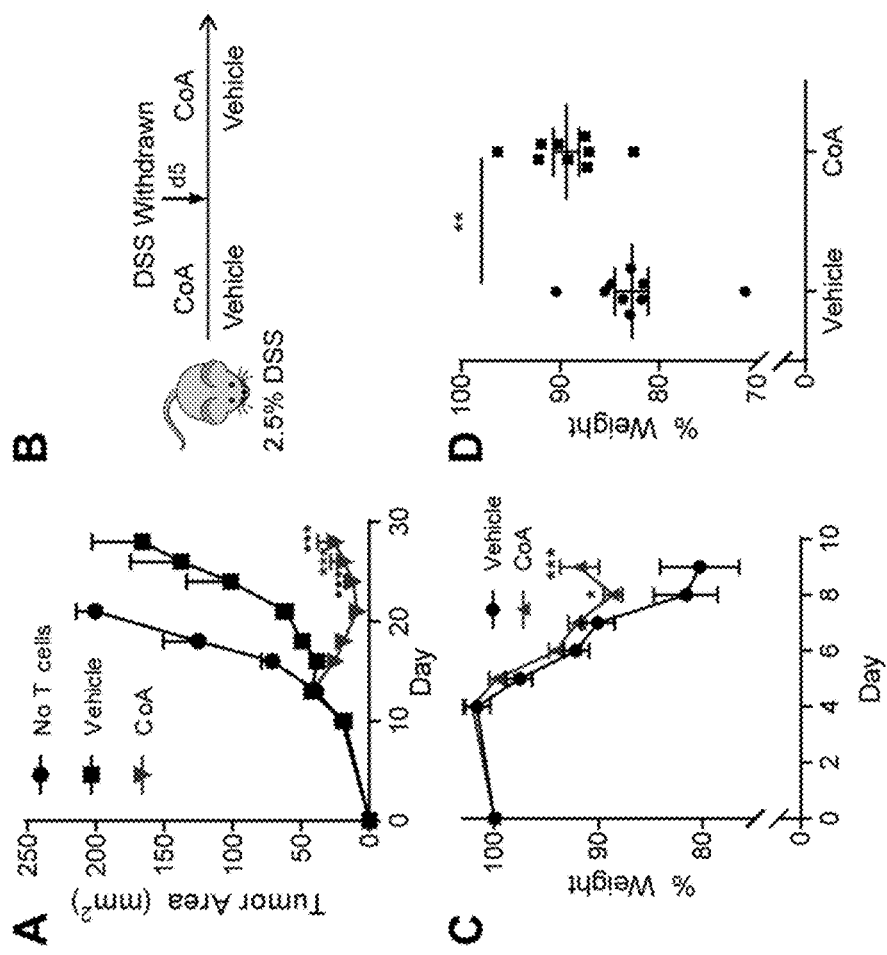
FIG. 4. CoA enhances anti-tumor function of T cells and protects against DSS colitis. (A). Mice were inoculated with B16-gp33 melanoma tumors and received an adoptive transfer of $0.5 \times 10^6$ CD8+P14-gp33 specific T cells activated in the presence of CoA or vehicle 10 days post tumor-inoculation. Results shown are mean tumor area (LxW) of 4-5 mice/group ±SEM. (B-D) Mice received 2.5% DSS in water for 5 days ±CoA or Vehicle. After 5 days, mice were switched to DSS-free water ±CoA or Vehicle (C) Mean % weight loss relative to day 0 weight of mice (n=5 mice/group ±SEM). (D) Cumulative mean % weight loss of DSS treated mice on day 8 pooled from 2 independent experiments (n=9 mice/group ±SEM). Results shown are (A,C) representative of at least 2 independent experiments or (D) pooled data from multiple independent experiments. (A,C) Repeated measures ANOVA with a Sidak test and (D) two-tailed t-test were used to calculate statistical significance relative to vehicle treated controls. *p<0.05, p<0.01, *p<0.001

Recently, it has been reported that CD8+ T cells with an increased capacity for OXPHOS are superior at mediating anti-tumor responses (23-25). Thus, we evaluated the role of CoA-treated cells in an in vivo mouse tumor model. Tumor-specific P14 CD8+ T cells, activated for three days in the presence of vehicle or CoA, were transferred into mice inoculated with B16-gp33 melanoma tumors. Mice that received CoA treated P14s demonstrated a significantly greater reduction in tumor growth compared to animals that received activated T cells treated with vehicle (FIG. 4A). We also tested CoA in a dextran sulfate sodium (DSS) colitis model (FIG. 4B) in which IL-22 has been shown to be protective (26). Indeed, mice administered oral CoA demonstrated a decrease in disease severity, suggesting that CoA has the potential for in vivo therapeutic applications (FIG. 4C,D).

Overall, we have demonstrated that Tc1, Tc17 and Tc22 CD8+ T cells subsets have distinct metabolic signatures. By further interrogating these metabolic differences, we found that a key distinction of Tc22 polarization is the requirement for OXPHOS. Importantly, we identified CoA as a molecule capable of promoting and enhancing Tc22 and Th22 polarization as a stand alone agent, mediated in part by oxidative HIF-1a signaling. Although previous studies have modified T cell lineage commitment by altering metabolism, these observations were still dependent on the presence of polarizing cytokines (13, 14). Here, we show that CoA alone is sufficient to induce Tc22 or Th22 generation. These data represent a paradigm shift in the generation of specific T cell subsets, as we suggest that the selective manipulation of cellular metabolism is sufficient to drive the induction of the Tc22 subset with potential therapeutic applications to treat diseases.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCE LIST

1. N. J. Maciver, R. D. Michalek, J. C. Rathmell, Metabolic regulation of T lymphocytes. Annu. Rev. Immunol. 31, 259-83 (2013).
2. E. L. Pearce, M. C. Poffenberger, C.-H. Chang, R. G. Jones, Fueling immunity: insights into metabolism and lymphocyte function. Science. 342, 1242454 (2013).
3. Y. Cao, J. C. Rathmell, A. N. Macintyre, Metabolic reprogramming towards aerobic glycolysis correlates with greater proliferative ability and resistance to metabolic inhibition in CD8 versus CD4 T cells. PLoS One. 9, 1-15 (2014).
4. R. Wang et al., The Transcription Factor Myc Controls Metabolic Reprogramming upon T Lymphocyte Activation. Immunity. 35, 871-882 (2011).
5. C. H. Chang et al., Posttranscriptional control of T cell effector function by aerobic glycolysis. Cell. 153, 1239-1251 (2013).
6. P.-C. Ho et al., Phosphoenolpyruvate Is a Metabolic Checkpoint of Anti-tumor T Cell Responses. Cell. 162, 1217-1228 (2015).
7. J. Blagih et al., The Energy Sensor AMPK Regulates T Cell Metabolic Adaptation and Effector Responses In Vivo. Immunity. 42, 41-54 (2015).
8. R. D. Michalek et al., Cutting edge: distinct glycolytic and lipid oxidative metabolic programs are essential for effector and regulatory CD4+ T cell subsets. J. Immunol. 186, 3299-303 (2011).
9. D. O'Sullivan et al., Memory CD8(+) T Cells Use Cell-Intrinsic Lipolysis to Support the Metabolic Programming Necessary for Development. Immunity. 41, 75-88 (2014).
10. E. L. Pearce et al., Enhancing CD8 T-cell memory by modulating fatty acid metabolism. Nature. 460, 103-107 (2009).
11. G. J. W. van der Windt et al., Mitochondrial Respiratory Capacity Is a Critical Regulator of CD8+ T Cell Memory Development. Immunity. 36, 68-78 (2012).
12. L. Z. Shi et al., HIF1alpha-dependent glycolytic pathway orchestrates a metabolic checkpoint for the differentiation of TH17 and Treg cells. J. Exp. Med. 208, 1367-76 (2011).
13. V. A. Gerriets et al., Metabolic programming and PDHK1 control CD4+ T cell subsets and inflammation. J. Clin. Invest. 125, 194-207 (2015).
14. L. Berod et al., De novo fatty acid synthesis controls the fate between regulatory T and T helper 17 cells. Nat. Med. 20, 1327-1333 (2014).
15. C. S. Hinrichs et al., Type 17 CD8+ T cells display enhanced antitumor immunity. Blood. 114, 596-9 (2009).
16. H.-W. Mittrucker, A. Visekruna, M. Huber, Heterogeneity in the differentiation and function of CD8+ T cells. Arch. Immunol. Ther. Exp. (Warsz). 62, 449-58 (2014).
17. S.-Y. Shin et al., An atlas of genetic influences on human blood metabolites. Nat. Genet. 46, 543-50 (2014).
18. B. Srinivasan et al., Extracellular 4'-Phosphopantetheine is a source for intracellular Coenzyme A synthesis. Nat. Chem. Biol. 11, 1-26 (2015).
19. G. M. Tannahill et al., Succinate is an inflammatory signal that induces IL-1p through HIF-1a. Nature. 496, 238-242 (2013).
20. M. A. Selak et al., Succinate links TCA cycle dysfunction to oncogenesis by inhibiting HIF-α prolyl hydroxylase. Cancer Cell. 7, 77-85 (2005).
21. S. A. Budda, A. Girton, J. G. Henderson, L. A. Zenewicz, Transcription Factor HIF-1A Controls Expression of the Cytokine IL-22 in CD4 T Cells. J. Immunol. 197, 2646-2652 (2016).
22. W. Y. Kim et al., Failure to prolyl hydroxylate hypoxia-inducible factor alpha phenocopies VHL inactivation in vivo. EMBO J. 25, 4650-62 (2006).
23. N. E. Scharping et al., The Tumor Microenvironment Represses T Cell Mitochondrial Biogenesis to Drive Intratumoral T Cell Metabolic Insufficiency and Dysfunction. Immunity. 45, 374-388 (2016).
24. J. G. Crompton et al., Akt inhibition enhances expansion of potent tumor-specific lymphocytes with memory cell characteristics. Cancer Res. 75, 296-305 (2015).
25. M. D. Buck et al., Mitochondrial Dynamics Controls T Cell Fate through Metabolic Programming. Cell. 166, 63-76 (2016).
26. L. A. Zenewicz et al., Innate and Adaptive Interleukin-22 Protects Mice from Inflammatory Bowel Disease. Immunity. 29, 947-957 (2008).
27. H. Pircher, K. Burki, R. Lang, H. Hengartner, R. M. Zinkernagel, Tolerance induction in double specific T-cell receptor transgenic mice varies with antigen. Nature. 342, 559-561 (1989).
28. A. Oxenius, M. F. Bachmann, R. M. Zinkernagel, H. Hengartner, Virus-specific MHC-class II-restricted TCR-transgenic mice: effects on humoral and cellular immune responses after viral infection. Eur. J. Immunol. 28, 390-400 (1998).
29. D. Dissanayake et al., Nuclear factor-KB1 controls the functional maturation of dendritic cells and prevents the activation of autoreactive T cells. Nat. Med. 17, 1663-7 (2011).
30. D. W. Huang, B. T. Sherman, R. A. Lempicki, Bioinformatics enrichment tools: paths toward the comprehensive functional analysis of large gene lists. Nucleic Acids Res. 37, 1-13 (2009).
31. D. W. Huang, B. T. Sherman, R. A. Lempicki, Systematic and integrative analysis of large gene lists using DAVID bioinformatics resources. Nat. Protoc. 4, 44-57 (2009).

The invention claimed is:

1. A method for inducing Tc22 lineage T cells from a population of $CD8^+$ T cells, the method comprising:

a) providing a population of $CD8^+$ T cells;

b) activating the population; and c) culturing or contacting the population of $CD8^+$ T cells with Coenzyme A.

2. The method of claim 1, wherein the activation comprises culturing or contacting the population with at least one of (i) anti-CD3 antibody and (ii) gp33 peptide from LCMV (KAVYNFATM) (SEQ ID NO. 1).

3. The method of claim 1, wherein the population of $CD8^+$ T cells is additionally cultured or contacted with TNF-α or IL-6.

4. The method of claim 1, wherein the population of $CD8^+$ T cells is additionally cultured or contacted with aryl hydrogen receptor (AhR) agonist.

5. The method of claim 4, wherein the aryl hydrogen receptor (AhR) agonist is 6-Formylindolo(3,2-b)carbazole (FICZ).

6. The method of claim 1, wherein the population of $CD8^+$ T cells is additionally cultured or contacted with anti-IFNγ antibody.

7. The method of claim 1, wherein the population of $CD8^+$ T cells is additionally cultured or contacted with anti-TGF-β antibody.

8. The method of claim 1, wherein the population of $CD8^+$ T cells is additionally cultured or contacted with succinate.

9. The method of claim 1, wherein the population of $CD8^+$ T cells is additionally cultured or contacted with pantothenate.

10. The method of claim 1, wherein the Tc22 lineage T cells are $CD8^+/IL\text{-}22^+/IL17^-/IFN\gamma^{low}$.

11. The method of claim 10, wherein the Tc22 lineage T cells are additionally IL-$4^-$, IL-$5^-$, IL-$9^-$, IL-$10^-$ and/or or IL-$13^-$.

12. The method of claim 10, wherein the Tc22 lineage T cells are additionally TNF-$\alpha^{hi}$ and/or IL-$2^{hi}$.

13. The method of claim 1, wherein step c) is performed before or after step b).

14. The method of claim 1, wherein step c) is performed simultaneously with step b).

15. A method of treating cancer or an inflammatory disease, comprising administering to the patient Coenzyme A treated Tcells.

16. The method of claim 15, wherein the inflammatory disease is a gastro-intestinal inflammatory disease.

17. The method of claim 16, wherein the gastro-intestinal inflammatory disease is colitis.

18. The method of claim 15, wherein the cancer comprises a cancerous tumor.

19. A method of treating a gastro-intestinal inflammatory disease, comprising administering to the patient Coenzyme A.

20. The method of claim 19, wherein the gastro-intestinal inflammatory disease is colitis.

21. A method of treating a cancerous tumor, comprising administering to the patient Coenzyme A.

* * * * *